US009271889B2

(12) United States Patent
Binder

(10) Patent No.: US 9,271,889 B2
(45) Date of Patent: Mar. 1, 2016

(54) INCAPACITATED PATIENT LIFT DEVICE

(71) Applicant: Daniel Keith Binder, Cody, WY (US)

(72) Inventor: Daniel Keith Binder, Cody, WY (US)

(73) Assignee: Daniel Keith Binder, Cody, WY (US)

( * ) Notice: Subject to any disclaimer, the term of this patent is extended or adjusted under 35 U.S.C. 154(b) by 143 days.

(21) Appl. No.: 13/872,659

(22) Filed: Apr. 29, 2013

(65) Prior Publication Data
US 2015/0136145 A1    May 21, 2015

Related U.S. Application Data

(60) Provisional application No. 61/649,598, filed on May 21, 2012.

(51) Int. Cl.
| | | |
|---|---|---|
| *A61G 7/10* | (2006.01) | |
| *A61F 5/03* | (2006.01) | |
| *A41D 13/00* | (2006.01) | |
| *A62B 35/00* | (2006.01) | |

(52) U.S. Cl.
CPC ............... *A61G 7/1023* (2013.01); *A61G 7/10* (2013.01); *A61G 7/1013* (2013.01); *A61G 7/1051* (2013.01); *A41D 13/0007* (2013.01); *A61F 5/03* (2013.01); *A62B 35/0006* (2013.01)

(58) Field of Classification Search
CPC ............. A61F 5/028; A61F 5/03; A61G 7/10; A61G 7/1013; A61G 7/1023; A61G 7/1049; A61G 7/1051; A41D 13/00; A41D 13/007; A62B 35/0006

USPC ......... 128/845, 846, 869, 874–876; 5/81.1 R, 5/81.1 T
See application file for complete search history.

(56) References Cited

U.S. PATENT DOCUMENTS

| | | | | |
|---|---|---|---|---|
| 5,361,418 | A | | 11/1994 | Luzenske |
| 5,514,019 | A | * | 5/1996 | Smith .............................. 441/88 |
| 6,050,364 | A | * | 4/2000 | Popall et al. ...................... 182/6 |
| 6,073,280 | A | * | 6/2000 | Farnum ............................ 5/89.1 |
| 6,578,210 | B2 | | 6/2003 | Erickson |
| 6,715,167 | B2 | * | 4/2004 | Wake ............................ 5/81.1 T |
| 7,490,610 | B2 | * | 2/2009 | Franklin ....................... 128/875 |
| 2008/0189853 | A1 | | 8/2008 | Felling |

OTHER PUBLICATIONS

International Search Report dated Sep. 23, 2014 from corresponding international application PCT/US2014/035879 USPTO PCT Division/ Authorized Officer Blaine R. Copenheaver.

* cited by examiner

*Primary Examiner* — Keri J Nelson

(57) ABSTRACT

A lifting system is provided for lifting a person who is incapacitated, where the lifting system includes a torso enclosure that may encase a substantial portion of the person's torso without requiring the person to slip one or both of their arms through the enclosure, and orthogonally-aligned structural straps positioned on the enclosure to stabilize and strengthen the enclosure during use, where portions of the straps are detached between two respective junction points to permit grasping of such straps by others when attempting to lift the incapacitated person.

4 Claims, 2 Drawing Sheets

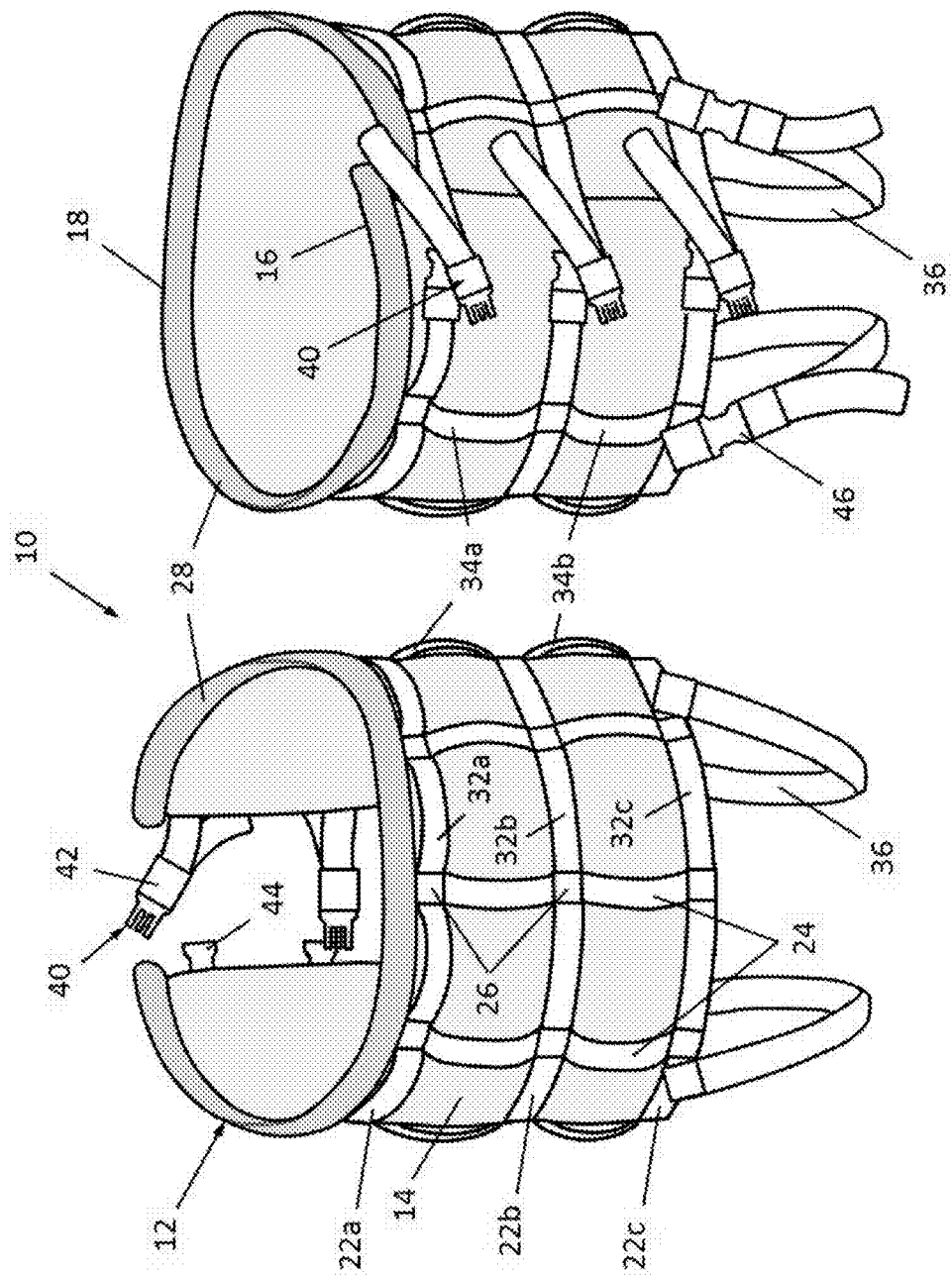

INCAPACITATED PATIENT LIFT DEVICE

RELATED APPLICATION

This application claims priority to provisional patent application U.S. Ser. No. 61/649,598 filed on May 21, 2012, the entire contents of which is herein incorporated by reference.

BACKGROUND

The embodiments herein relate generally to devices for assisting the lifting of persons who are temporarily or permanently incapacitated, and must be moved from a prone or sitting position to an upright or higher elevation. In that regard, harnesses have been used for years to lift persons as well as animals. Harnesses generally consist of one or more straps that may be placed around the person or animal and secured in place to "lift" the person or animal from one position to another.

Other harness-related devices have been disclosed as well. For example, the reader is directed to such prior references as U.S. Pat. No. 5,269,324, entitled Patient lifting harness and method of use; U.S. Pat. No. 5,647,378, entitled Invalid support belt, U.S. Pat. No. 5,896,859, entitled Transfer belt, U.S. Pat. No. 6,122,778, entitled Lift vest, U.S. Pat. No. 6,581,222, entitled Lifting sling, U.S. Pat. No. 7,627,912 entitled Portable patient transfer system, U.S. Pat. No. 7,945,975, entitled Patient assistance device, and Design Pat. No. D636,964, entitled Patient assistance vest. It is not known whether any of these devices have been commercialized or to any level of success.

A search of the internet has revealed devices being commercialized by Kendrick, known as the Kendrick Extrication Device, and a device by Smart Life Systems. None of these devices, including those disclosed in the references cites above, work as efficiently or as effectively as they should for various reasons. Indeed, emergency medical personnel have commented at the time of this application on the lack of adequate patient lifting devices in the marketplace given the variety of circumstances encountered by EMTs. Embodiments of the present invention address at least some of the disadvantages of the prior devices.

SUMMARY

In one embodiment, a lifting system is provided for permitting emergency personnel to lift a person who is presently unable to lift themselves. The lifting system may comprises a torso enclosure configured to encase a substantial portion of the person's torso without requiring the person to slip one or both of their arms through the enclosure, the enclosure comprising a first axis and an orthogonally-oriented second axis. Embodiments also comprise a plurality of orthogonally-aligned structural straps positioned on the enclosure to stabilize and strengthen the enclosure during use. In one variation, a first set of the plurality of orthogonally-aligned structural straps is positioned substantially parallel to the first axis of the enclosure and a second set is positioned substantially parallel to the second axis of the enclosure.

Preferably, at least some of the orthogonally-aligned straps are affixed at the junction of such straps to each other, and also to the enclosure at the location of the junction. At least some of the plurality of straps positioned substantially parallel to the second axis of the enclosure comprise a first set of detached strap portions, where the detached portions are positioned between two respective junction points to permit emergency personnel to grasp such straps when attempting to lift the incapacitated person. It is contemplated that at least some of the plurality of straps positioned substantially parallel to the first axis of the enclosure comprise a first set of detached strap portions.

In some embodiments, a lifting system comprises a plurality of leg straps secured to the enclosure, where one or both of the leg straps are configured to wrap around a portion of the person's leg so as to minimize the movement of the enclosure relative to the person during attempts to lift the person, thereby making the lifting process more efficient when compared to enclosures that slide to an undesired degree. The legs straps may be detachable from the enclosure, if so desired. Preferably, but optionally, the enclosure may comprise an upper collar surrounding a substantial portion of the enclosure, where the upper collar provided cushion against forceful engagement of the enclosure under the arms of the person with minimal discomfort.

BRIEF DESCRIPTION OF THE FIGURES

The detailed description of some embodiments of the invention will be made below with reference to the accompanying figures, wherein like numerals represent corresponding parts of the figures.

FIGS. 1A and 1B show a perspective schematic of one embodiment of the present inventive patient assist device;

DETAILED DESCRIPTION OF CERTAIN EMBODIMENTS

Figure 2:
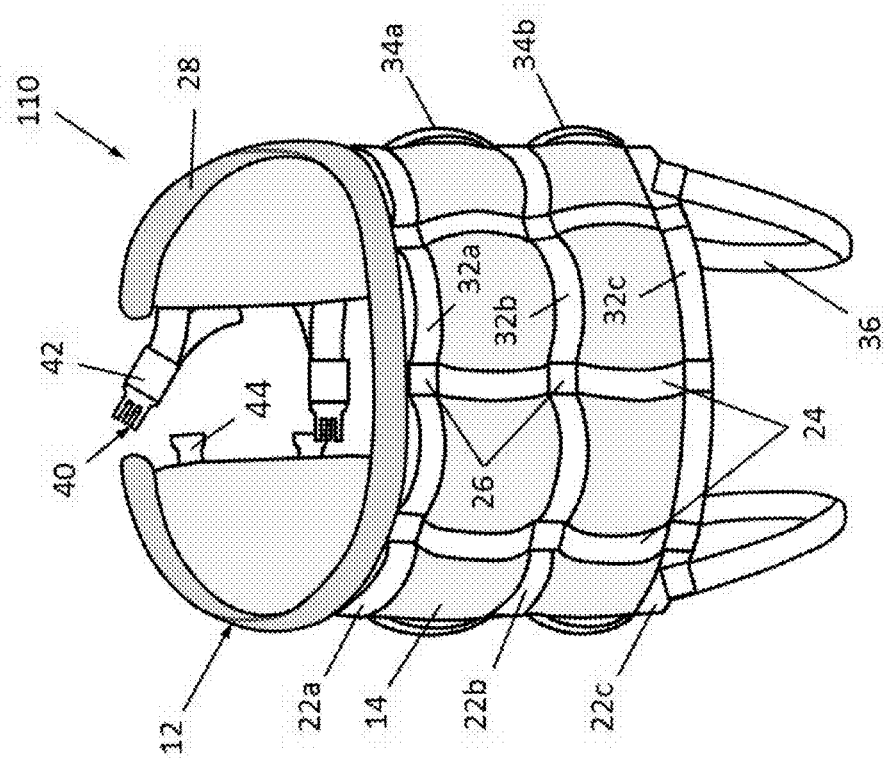
FIG. 2 shows a schematic view of an alternative embodiment.

By way of example, and referring to FIGS. 1A and 2B, one embodiment of a patient assist device 10 of the present invention comprises a lifting device 12 that may be enveloped about the torso of an incapacitated individual easily for lifting the individual from a first lower position (e.g., prone or sitting on the floor) to a second higher position (e.g., standing or sitting in a chair or bed). Incapacitated individuals tend to present to those tasked with assisting such individuals, such as EMTs, what is colloquially but literally dead weight. When certain incapacitated individuals are unable to assist at all in the lifting process, such individuals can be very heavy to lift, even for multiple persons who try to assist in lifting the individual. Part of the benefits of embodiments described herein, and variations thereof, is the provision of multiple gripping positions around the patient assist device 10, and the ease to which the patient assist device may be applied to the incapacitated individual.

In that regard, embodiment 10 comprises a torso enclosure 14 that is configured to be wrapped around the torso of the incapacitated individual. The torso enclosure 14 preferably has an anterior portion 16 and a posterior portion 18, and may be made of one or more of a number of materials sufficiently sturdy to bear the forces applied in lifting the individual. For example, it may be made from canvas, denim, or the like, and may include a layer of cushioning within or without the enclosure if so desired. In one embodiment, the torso enclosure 14 comprises generally orthogonally-placed webbing in the form of structural straps affixed to the torso enclosure 14, again sufficiently rigidly affixed to withstand the forces associated with lifting the individual. In one variation, a plurality of horizontal structural straps 22 oriented in first axis of the torso enclosure 14 and a plurality of vertical structural straps 24 oriented in a second axis generally orthogonal to the first axis. The terms horizontal and vertical are merely by example with respect to a lifting device 12 sitting upright as shown in FIGS. 1A and 1B, and are not limiting in the variation of placement of webbing to the torso enclosure 14. Indeed, the axes of the first and second sets of structural straps 22, 24, may be oriented at an angle from the longitudinal axis of the lifting device 12, if so desired.

Preferably, the orthogonally-oriented straps 22, 24 are secured to each other and to the torso enclosure 14 at strap junction points 26. Such junction points may reflect overlapping of one strap across another strap, or it may reflect a discrete component to which each orthogonally-oriented strap is secured. Numerous configurations are contemplated for joining the two sets of straps together and securing the straps (at least in part as described below) to the enclosure 14, including via mechanical affixation or chemical adhesion. The straps 22, 24 may be made of heavy-duty canvas or nylon fabric, for example, and may be sewn to each other and/or the torso enclosure 14. Other materials are contemplated for the straps 22, 24.

In the embodiment of FIGS. 1A and 1B, for example only, there are three horizontally-oriented sets of straps 22 (22a, 22b, 22c) traversing at least a portion if not the entirety of the torso enclosure 14. By example only, this particular embodiment comprises a larger number of vertically-oriented sets of straps 24 spaced radially about the torso enclosure 14 at selected and/or desired spacing, depending upon the need or desire of the manufactures and/or consumers. As is shown, the two sets of straps come together at the plurality of strap junction points 26 positioned about the enclosure 14.

If desired, some embodiments of the patient assist devices may comprise a cushioned collar 28 positioned in annular fashion about one end of the lifting device 12. It is contemplated that when embodiments of the patient assist device 10 are positioned on the incapacitated person and those aiding the person lift that person, there will be a tendency of the lifting device 12 to move up the person's torso to the underarm position. Of course, the enclosure 14 may be tightened sufficiently to avoid movement, but that may require the enclosure being too tight for the comfort of the patient. By providing an optional cushioned collar 28, additional comfort may be provided to the patient during the lifting process so that the enclosure pushes against the person's underarms with great cushioning effect. The cushion may be padding of one of numerous materials, or padding within a fabric covering, and any other similar arrangements.

One beneficial feature of embodiments of the present invention is the provision of grips at a plurality of locations about the torso enclosure 14. In that regard, certain portions of the straps 22, 24 between junction points 26 may be left unsecured to the enclosure 14, while others remain tightly secured to the enclosure 14. With reference to FIG. 1A, for example only, the upper horizontally-oriented portions 32a of row 22a are provided detached from the enclosure 14 between junction points 26. In contrast, portions 32b and 32c of rows 22b, 22c, respectively, are provided in secure attachment to the enclosure. Likewise, and again by example, each of the plurality of portions 34a and 34b of vertically-oriented straps 24 are left detached from the enclosure 14 between junction points 26. Each detached portion, whether horizontal or vertical, presents a place where a person aiding in the lifting of a person wearing the patient device 12 can grab the device for purposes of lifting the incapacitated person.

The combination of orthogonally-oriented gripping portions provides for a more effective and efficient lifting device because those tasked with lifting the incapacitated person have a number of possible gripping positions. That is advantageous because the number of persons aiding in the lifting is not known; nor is the height of the persons aiding. For example, a tall assisting person might find it more appropriate to grasp vertical grips 34a, while a shorter assisting person might find it more appropriate to grasp vertical grips 34b.

An optional feature of embodiments of the present invention comprise leg straps 36, preferably one for each leg. The leg straps 36 may be made of any desired materials, as described above for the webbing straps, and are preferably configured to comfortably wrap around the upper portion of the incapacitated person's legs both to secure the lifting device 12 to the person and also to restrain relative movement of the lifting device 12 on the person during the lifting process.

As viewed from the anterior portion 16 of the enclosure 14 in FIG. 1B, the horizontal straps 22 may be secured at respective ends via fasteners 40. Such fasteners may be one or more of numerous types of fasteners that permit engagement of the strap ends securely, but permits quick connect and disconnect functionality. In one embodiment, fasteners 40 comprises a male coupler 42 that slideably engages and locks into female coupler 44. Sufficient strap material is provided to permit adjustment of the tightness of the torso enclosure 14 about the incapacitated person. Likewise, fasteners 46 may be provided on the leg straps 36 for quick connect and disconnect functionality.

Figure 3:
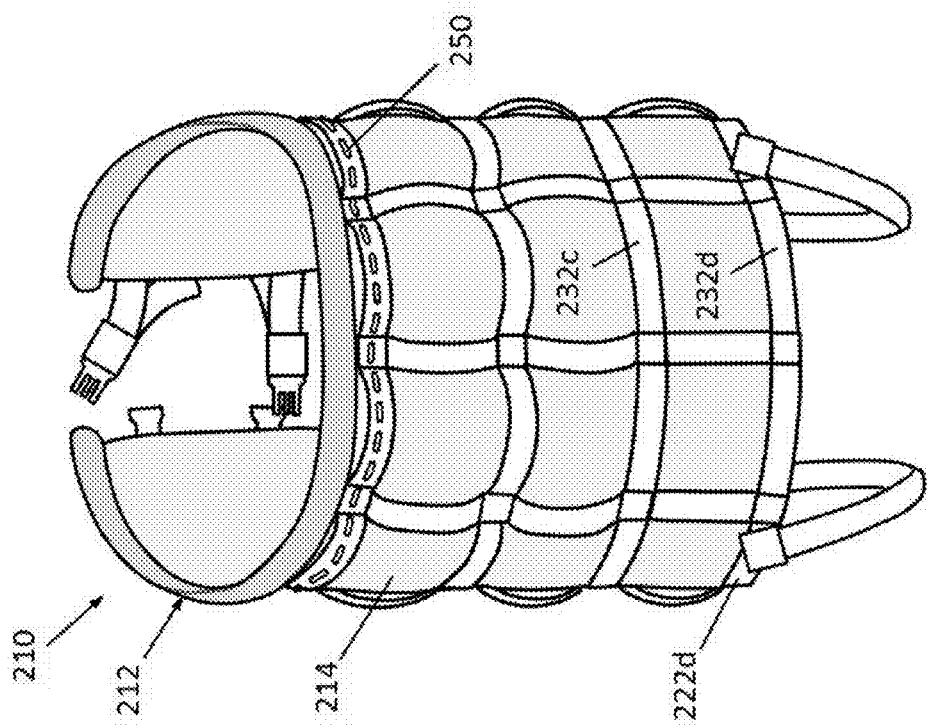
FIG. 3 shows a schematic view of another alternative embodiment.

Many variations are contemplated for the patient assistance embodiments herein. For example, with reference to FIG. 2, patient assistance embodiment 110 comprises lifting device 12 where portions 32b of the second horizontal row 22b of straps 22 may be detached to provide yet additional grips. With reference to FIG. 3, yet another alterative embodiment 210 comprises a lifting device 212 comprising a torso enclosure 214 that is longer than those shown in the earlier figures. Such a longer lifting device 212 may be more appropriately suited for an incapacitated person who is very tall or who has a particularly long torso. In that regard, one or more additional rows of horizontal straps (e.g., 222d) may be provided where portions 232d of straps 222d may be securely attached to the torso enclosure 214. In this particular example of a longer embodiment 210, it is illustrated that the upper two rows have strap portions detached to provide grips, while portions 232c and 232d remain attached. Likewise, the upper two portions of the vertically-oriented straps may be detached while the lower portion remains attached. Variations on any of these is contemplated.

Another feature that is contemplated is the provision of additional force-bearing capacity to the lifting devices. For example, if desired, a chain 250 may be provided encircling the torso enclosure 214. In one embodiment, the chain is provided co-linearly with one of the horizontally-oriented straps, in this case the upper one, but it may be placed in other positions as well. It is contemplated that the lifting device be provided with a chain 250 already secured to the torso enclosure 214, or may be feed through loops provided on the torso enclosure to be added in real-time where those tasked with lifting a person believe that the added benefit of additional-force bearing structure is desired. The chain may be made of one or more of a number of sturdy materials designed to bear dead weight forces of heavy individuals, including metal, Kevlar™ fabric, carbon fiber, etc. The chain or other force bearing structure may be applied to lifting devices of any size, including the larger examples of FIG. 3, and the smaller examples of FIGS. 1A and 1B.

One benefit of the configurations of the embodiments herein if that the lifting device need not be placed about the incapacitated person's arms, such as the vests used in the prior art. Such a configuration saves time in applying the lifting device to the patient for use under exigent circumstances or within minimal inconvenience to the patient.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A lifting system for use by an emergency medical technician in assisting the moving or lifting of a disabled individual, the lifting system comprising a sleeve-less torso enclosure, the sleeve-less torso enclosure comprising:

a pad having an inner surface for engaging the individual and an outer surface for access by the emergency medical technician, the pad comprising first and second ends and first and second sides positioned generally orthogonally to the first and second ends, where the first and second ends are configured to be wrapped around the individual's torso so that the torso enclosure can be positioned in a wrapped configuration, the torso enclosure defining an opening between the first and second ends of the pad when the length of the pad from first end to second end is smaller than the circumference of the individual's torso, and wherein the first and second ends of the pad are configured to overlap when the length of the pad from first end to second end is larger than the circumference of the individual's torso;

first, second and third structural straps secured to the pad, at spaced positions generally parallel to the first and second sides of the pad, the first structural strap positioned proximate the first side of the pad, the second structural strap positioned proximate the second side of the pad, and the third structural strap positioned between the first and second structural straps and generally parallel therewith, the three structural straps being affixed to the pad between the first and second ends of the pad such that at least one of the structural straps comprises a plurality of first lifting portions; and a plurality of lifting straps secured to the pad, each lifting strap positioned generally orthogonally to the first, second and third structural straps and extending between at least the first and second structural straps, each lifting strap intersecting with and affixed to the first, second and third structural straps to define intersection areas that are affixed to the pad, at least two of the plurality of lifting straps each comprising a plurality of second lifting portions each defined by a segment of the lifting strap not affixed to the pad and between adjacent intersection areas associated with that lifting strap and two structural straps, each of the plurality of first lifting portions being defined by a segment of the at least one of the structural straps not affixed to the pad and between adjacent intersection areas associated with the at least one of the structural straps and two adjacent lifting straps such that the first lifting portions are generally orthogonally-positioned with respect to the second lifting portions, the second lifting portions being configured such that if two from the same lifting strap are engaged simultaneously, the load is distributed to each of the first, second and third structural straps proximal such lifting strap, wherein a first and second end of each structural strap comprises a mating adjustable fastener in which the fastener of one end is configured to engage the mating fastener of the other end of the same structural strap so that when fastened and tightened when the torso enclosure is wrapped around the torso of an individual the torso enclosure can resist upward movement relative to the individual's torso, and wherein the first and second orthogonally-positioned lifting portions provide alternative lifting positions for emergency medical technicians in which some lifting portions are generally vertically-oriented and some lifting portions are generally horizontally-oriented when the torso enclosure is secured about the torso of the individual and the individual's torso is in a generally vertical or horizontal orientation.

2. The lifting system of claim 1, further comprising a plurality of leg straps secured to one side of the pad, each leg strap comprising an adjustable fastener configured to permit an emergency medical technician to tighten the leg straps to minimize upward movement of the torso enclosure when upward force is applied by the emergency medical technician on the torso enclosure thereby minimizing injury to the individual's underarm area from the compression of the torso enclosure against the individual's underarm area.

3. The lifting system of claim 1, wherein the torso enclosure further comprises a collar along a substantial portion of one side of the pad, the collar providing cushion against forceful engagement of the enclosure under the arms of the person being lifted with minimal discomfort.

4. The lifting system of claim 1, further comprising a chain for bearing significantly-heavy individuals whose weight could damage the lifting system during use.

* * * * *